United States Patent
Yick

(10) Patent No.: US 9,504,539 B2
(45) Date of Patent: Nov. 29, 2016

(54) SELF-LIGATING ORTHODONTIC BRACKET

(71) Applicant: 3M INNOVATIVE PROPERTIES COMPANY, St. Paul, MN (US)

(72) Inventor: Lee C. Yick, Placentia, CA (US)

(*) Notice: Subject to any disclaimer, the term of this patent is extended or adjusted under 35 U.S.C. 154(b) by 15 days.

(21) Appl. No.: 14/416,505

(22) PCT Filed: Jul. 15, 2013

(86) PCT No.: PCT/US2013/050545
§ 371 (c)(1),
(2) Date: Jan. 22, 2015

(87) PCT Pub. No.: WO2014/018298
PCT Pub. Date: Jan. 30, 2014

(65) Prior Publication Data
US 2015/0182307 A1 Jul. 2, 2015

Related U.S. Application Data

(60) Provisional application No. 61/674,583, filed on Jul. 23, 2012.

(51) Int. Cl.
*A61C 7/30* (2006.01)
*A61C 7/12* (2006.01)
*A61C 7/28* (2006.01)

(52) U.S. Cl.
CPC ............... *A61C 7/30* (2013.01); *A61C 7/125* (2013.01); *A61C 7/285* (2013.01)

(58) Field of Classification Search
CPC ............ A61C 7/14; A61C 7/12; A61C 7/28; A61C 7/285; A61C 7/287; A61C 7/34; A61C 7/148; A61C 7/145; A61C 7/30; A61C 7/125

USPC .......................................... 433/8, 10, 11, 13
See application file for complete search history.

(56) References Cited

U.S. PATENT DOCUMENTS 4,536,154 A 8/1985 Garton, Jr.
5,078,596 A 1/1992 Carberry
(Continued)

FOREIGN PATENT DOCUMENTS

EP 1836990 9/2007
WO WO 2011/091397 7/2011
WO WO 2014/018298 1/2014

OTHER PUBLICATIONS

International Search report for PCT International Application No. PCTUS2013/050545 mailed on Oct. 25, 2013, 4 pgs.

*Primary Examiner* — Nicholas Lucchesi

(57) ABSTRACT

An aesthetic ceramic material is combined with a resilient metal to obtain an aesthetic self-ligating appliance with an easily operable latch mechanism. The appliance uses a door assembly that includes a ceramic ligating cover coupled to a resilient clip pivotable about a hinge mechanism. The clip functions as a latch to reversibly secure the clip and ligating cover to the appliance and retain an archwire in an archwire slot, and is capable of providing active ligation whereby the clip elastically deflects while directly or indirectly providing a continuous force to the archwire. Advantageously, the clip has a configuration that allows an orthodontic practitioner to pivot open the door assembly with minimal force while preventing the inadvertent opening of the door assembly as a result of normal forces applied by the archwire against the door assembly during the course of treatment.

21 Claims, 7 Drawing Sheets

(56) References Cited

U.S. PATENT DOCUMENTS

| | | | |
|---|---|---|---|
| 5,254,002 A | 10/1993 | Reher | |
| 5,439,379 A | 8/1995 | Hansen | |
| 5,474,445 A * | 12/1995 | Voudouris | A61C 7/285 433/10 |
| 5,685,711 A * | 11/1997 | Hanson | A61C 7/285 433/11 |
| 6,257,883 B1 * | 7/2001 | Voudouris | A61C 7/02 433/11 |
| 6,648,638 B2 | 11/2003 | Castro | |
| 6,964,565 B2 * | 11/2005 | Abels | A61C 7/285 433/10 |
| 7,094,052 B2 * | 8/2006 | Abels | A61C 7/146 433/10 |
| 7,234,935 B2 * | 6/2007 | Abels | A61C 7/285 433/10 |
| 7,247,019 B2 * | 7/2007 | Abels | A61C 7/285 433/10 |
| 7,611,352 B2 * | 11/2009 | Abels | A61C 7/125 433/10 |
| 7,695,277 B1 * | 4/2010 | Stevens | A61C 7/285 433/11 |
| 2002/0110775 A1 | 8/2002 | Abels | |
| 2002/0110778 A1 * | 8/2002 | Abels | A61C 7/125 433/11 |
| 2004/0157186 A1 | 8/2004 | Abels | |
| 2005/0019719 A1 | 1/2005 | Hanson | |
| 2005/0186525 A1 | 8/2005 | Abels | |
| 2006/0199137 A1 * | 9/2006 | Abels | A61C 7/12 433/11 |
| 2008/0241782 A1 | 10/2008 | Abels | |
| 2010/0055626 A1 | 3/2010 | Endou | |
| 2010/0159411 A1 * | 6/2010 | Oda | A61C 7/02 433/11 |
| 2011/0039225 A1 | 2/2011 | Hagelganz | |
| 2011/0183280 A1 | 7/2011 | Cosse | |
| 2012/0064476 A1 * | 3/2012 | Sabilla | A61C 7/28 433/11 |
| 2015/0173858 A1 * | 6/2015 | Dupray | A61C 7/143 433/11 |

\* cited by examiner

SELF-LIGATING ORTHODONTIC BRACKET

CROSS REFERENCE TO RELATED APPLICATIONS

This application is a national stage filing under 35 U.S.C. 371 of PCT/US2013/050545, filed Jul. 15, 2013, which claims priority to U.S. Provisional Application No. 61/674,583, filed Jul. 23, 2012, the disclosures of which are incorporated by reference in their entirety herein.

FIELD OF THE INVENTION

Provided are appliances useful for orthodontic treatment and methods related thereof. In particular, the provided appliances and methods relate to self-ligating orthodontic appliances.

BACKGROUND

Orthodontic appliances are devices used in the professional supervision, guidance and correction of a patient's malpositioned teeth. The many benefits of orthodontic treatment include the attaining and maintaining of a proper bite function, enhancement of facial aesthetics, and easier maintenance of dental hygiene. Orthodontic appliances are placed in mechanical engagement with the patient's teeth and apply gentle mechanical forces that gradually move the teeth toward corrected positions to achieve a proper bite (or occlusion).

A very common type of orthodontic treatment uses tiny slotted appliances called orthodontic brackets, which are adhesively attached to either the front or back surfaces of the patient's teeth. To move the teeth within an upper or lower arch, a resilient arch-shape wire ("archwire") is mechanically engaged, or "ligated," into the slot of each bracket. The ends of the archwire are generally captured in appliances called molar tubes, which are bonded to the patient's molar teeth. As the archwire slowly returns to its original shape, it acts as a track that guides the movement of teeth toward their desired positions. The brackets, tubes, and archwire are collectively known as "braces."

Conventional brackets are ligated to the archwire with the help of opposing tiewings, which are cleat-like projections on the bracket body. After the archwire is placed in the archwire slot, either a tiny elastomeric "O"-ring ligature or a metal ligature wire is looped over the archwire and beneath the undercut portions of tiewings located on opposite sides of the archwire slot. By tightly encircling the undercut portions of the tiewings, the ligature (or ligature wire) can secure the archwire within the archwire slot of each bracket, while still allowing the archwire to slide longitudinally along the slot. Depending on the relative sizes and shapes of the archwire and the slot, it is possible to achieve a precise mechanical coupling between the two bodies. This enables the practitioner to control the position and orientation of each individual tooth in the arch.

Both of the ligating mechanisms above have certain drawbacks. For example, the frictional contact between O-ring ligatures and the archwire can increase resistance to archwire sliding within the slot. Moreover, the elastic properties of these ligatures can degrade over time, resulting in unpredictable sliding mechanics. While these ligatures can be made from translucent polymers for aesthetic treatment, these same ligatures also tend to stain in the presence of dark-colored foods and liquids. Ligature wire poses its own problems, since the process of tying and trimming the wire can be cumbersome and time-consuming for the orthodontic professional. Being made of metal, ligature wire is also considered non-aesthetic.

Self-ligating brackets present a solution to at least some of the above problems. These appliances generally use a clip, spring member, door, shutter, bail, or other ligation mechanism built into the bracket itself to retain the archwire in the slot, thereby obviating use of a separate ligature. Several advantages can derive from the use of these ligation mechanisms. For example, these appliances can decrease friction between the archwire and the bracket compared with appliances ligated with elastomeric ligatures, potentially providing faster leveling and aligning of teeth in early stages of treatment. Depending on the mechanism, these appliances can also simplify the installation and removal of an archwire, significantly reducing chair time for the treating professional. Finally, self-ligating brackets can provide better hygiene than conventional brackets, which use elastomeric ligatures and ligature wires that can trap food and plaque.

SUMMARY

Technical challenges stand in the way of achieving an aesthetic self-ligating bracket that is both easy to use and reasonably capable of being manufactured. For one, the materials used in a clip, spring member, door, bail, or other ligation mechanism are typically metallic, and strongly contrast with the natural color of teeth. While polymeric materials are aesthetic and can be configured for this function, polymers are generally soft, vulnerable to mechanical wear and fatigue, and stain easily during the course of treatment. Ceramic materials have long been known to provide good strength, resistance to staining, and excellent aesthetics. However, these materials tend to be brittle, can be difficult to machine and assemble, and do not have the resiliency needed for most ligation mechanisms. Molded ceramic parts are subject to further limitations, since such parts generally need to be readily removable from the mold.

Aesthetic self-ligating appliances, particularly those made from ceramic materials, are also generally "passive" ligation devices. In passive ligation, the archwire is held captive within the slot but allowed to "float" freely within the archwire slot. Such a configuration can provide low friction between archwire and appliance but the freedom of movement within the archwire slot can compromise control. By contrast, in "active ligation," the appliance imparts a continuous force urging the archwire toward the bottom wall or side wall of the slot. Active ligation can be desirable in some stages of treatment, particularly when using square and rectangular archwires, because "actively" seating these wires into the bracket slot can improve transmission of torque and rotational forces to the teeth.

The aforementioned limitations can be addressed by combining different materials, each having certain preferred mechanical properties, to obtain an active self-ligating appliance with an easily operable ligation mechanism and superior aesthetics. The appliance uses a door assembly that includes a ceramic ligating cover coupled to a resilient clip pivotable about a hinge mechanism. The clip functions as a latch to reversibly secure the clip and ligating cover to the appliance and retain an archwire in an archwire slot. Alone or in combination with associated components of the door assembly, the clip can further provide for active ligation whereby the clip elastically deflects while imparting a continuous, positive force to the archwire. Advantageously, the clip can display force characteristics allowing an orthodontic practitioner to pivot open the door assembly easily while also preventing the inadvertent opening of the door assembly as a result of normal forces applied by the archwire against the door assembly during the course of treatment.

In one aspect, an orthodontic appliance is provided. The orthodontic appliance comprises: a base having a outer surface adapted for bonding to a tooth; a body extending outwardly from the base in a direction away from the outer surface of the base and having an elongated archwire slot therein extending along a generally mesial-distal direction, the archwire slot having a bottom wall and a pair of sidewalls; a hinge coupled to the body and having a hinge axis extending along a generally mesial-distal direction; and a door assembly comprising: a ceramic ligating cover; and a resilient clip coupled to one or both of the ligating cover and the hinge, wherein the door assembly is pivotable along the hinge axis between an open position allowing access to the archwire slot and a closed position obstructing access to the archwire slot, the ligating cover substantially obscuring the clip when the appliance is in its closed position.

As an option, the orthodontic appliance further comprises an air gap extending between the ligating cover and the clip, the air gap providing space for the clip to elastically deform in a direction away from the bottom wall of the archwire slot in active ligation.

In another aspect, a method of activating an archwire in an orthodontic appliance is provided, the orthodontic appliance having a body with an elongated archwire slot having a bottom wall and pair of side walls therein and a latched door assembly including a resilient clip provided alongside a ligating cover presenting an air gap therebetween, and a hinge interconnecting the body and door assembly. The method comprises: placing the archwire in the archwire slot; and pivoting the door assembly about the hinge until the clip latches to the body, the clip resiliently deflecting into the air gap while the clip applies a compressive force urging the archwire towards the bottom of the archwire slot.

DEFINITIONS

As used herein:

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's lips or cheeks.

"Lingual" means in a direction toward the patient's tongue.

DETAILED DESCRIPTION

The sections below describe illustrative embodiments directed to self-ligating orthodontic appliances and methods related thereto. These embodiments are exemplary and accordingly should not be construed to unduly limit the invention. For example, it is to be understood that one of ordinary skill can adapt the disclosed appliances and methods for attachment to either the labial or lingual surfaces of teeth, to different teeth within the same dental arch (for example, corresponding appliances on mesial and distal halves of the dental arch), or to teeth located on either the upper or lower dental arches.

The appliances and methods described herein may optionally be customized to the individual patient undergoing treatment. Material and dimensional specifications could also vary from those disclosed herein without departing from the scope of the claimed invention. Unless otherwise specified, the provided appliances and components could be constructed of any of a variety of metal, ceramic, polymeric, and composite materials known to those skilled in the art. Further, unless otherwise indicated, dimensions associated with the appliances and their components are not critical and the accompanying drawings are not necessarily drawn to scale.

Figure 1:
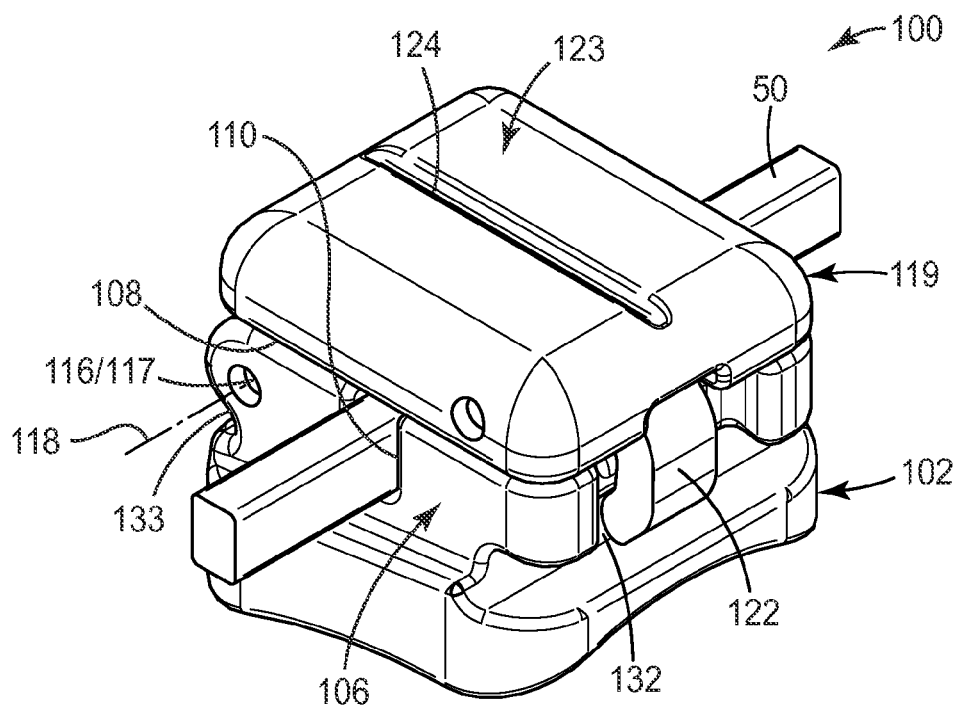
FIG. 1 is a perspective view of an orthodontic assembly including an appliance and archwire segment according to one embodiment, looking toward its facial, mesial, and gingival sides.

An aesthetic orthodontic bracket according to one embodiment is shown in FIGS. 1-6 and designated by the numeral 100. In each of these figures, the appliance 100 is shown engaged to a segment of an exemplary archwire 50. Referring to FIG. 1, the appliance 100 has a base 102 having an outer surface 104 adapted for adhesive bonding to a patient's tooth. Preferably and as shown, the outer surface 104 is concave and substantially conforms to the convex outer surface of the tooth.

In preferred embodiments, the outer surface 104 includes metal mesh, holes, bumps, recesses, undercuts, a microetched surface, glass grit, bonded particles, an organosilane treated surface, or any other known mechanical or chemical modification to enhance adhesive bonding between the base 102 and the underlying tooth. Alternatively, the base 102 could also have a banded configuration in which the base 102 fully encircles the tooth to provide an even stronger bond.

Extending outwardly from the base 102 in a direction away from the outer surface 104 of the base 102 is a body 106. Optionally and as shown, the base 102 and body 106 are integral components made from an aesthetic material. For example, the base 102 and body 106 could be machined or molded from a polymeric material as disclosed in U.S. Pat. No. 4,536,154 (Garton, et al.), a ceramic material such as a fine-grained polycrystalline alumina as disclosed in U.S. Pat. No. 6,648,638 (Castro, et al.), or a polymer-ceramic composite such as glass-fiber reinforced polymeric composites as disclosed in U.S. Pat. No. 5,078,596 (Carberry, et al.) and U.S. Pat. No. 5,254,002 (Reher, et al.).

The body 106 has a facial surface 108 and an elongated archwire slot 110 located extending in a generally mesial-distal direction across the facial surface 108. Referring now to the mesial view in FIG. 5, the archwire slot 110 has a bottom wall 112 along with occlusal and gingival side walls 114. As shown, the archwire 50 is received in the archwire slot 110 and has a generally rectangular cross-section that substantially corresponds with walls 112, 114 of the archwire slot 110. Filling the archwire slot, as is shown here, can provide for a precise coupling between the archwire 50 and appliance 100 and give the treating practitioner a high degree of control over the movement of teeth. Of course, other archwire geometries can be used.

Figure 5:
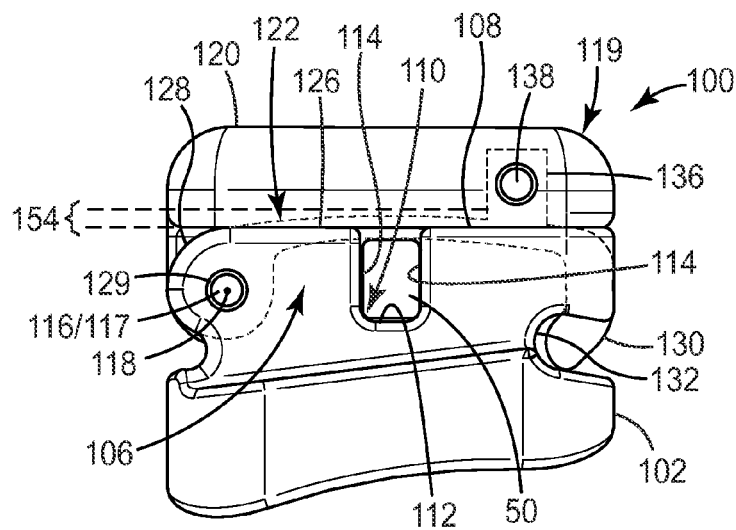
FIG. 5 is a mesial view of the assembly of FIGS. 1-4, looking toward its mesial side, with some internal components and features shown in phantom.
Figure 6:
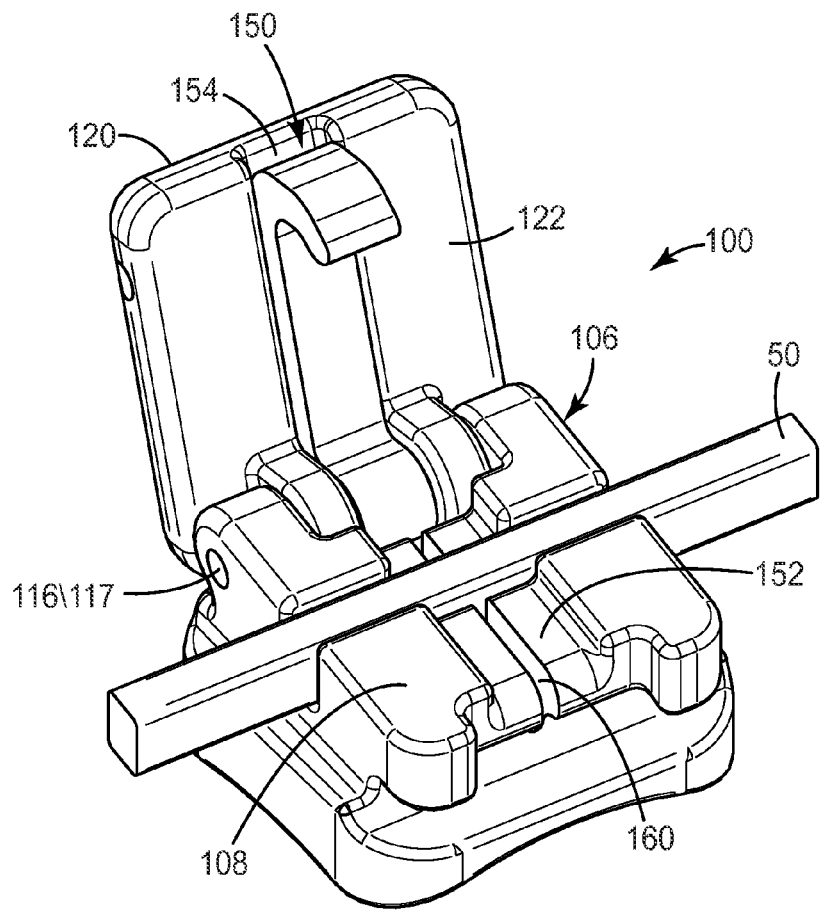
FIG. 6 is a perspective view of the assembly of FIGS. 1-5, showing the appliance in an opened configuration and looking toward its facial, mesial, and gingival sides.

As shown in FIGS. 1, 5, and 6, a hinge 116 is coupled to the body 106, and a door assembly 119 is coupled to the hinge 116 whereby the archwire 50 is held captive in the archwire slot 110. In the configuration shown, the archwire 50 is securely ligated to the appliance 100 such that the archwire 50 will not become accidently dislodged as a result normal chewing and brushing activity that occurs in a patient's mouth. However, the archwire 50 can, and should, be capable of sliding along the length of the archwire slot 110, thereby allowing the archwire 50 to function as a track that guides the movement of maloccluded teeth. Such sliding is especially important as the teeth unravel during the leveling and aligning stages of treatment.

The appliance 100 has a configuration that provides for traditional methods of ligation. As shown in FIG. 1, a gingival undercut 132 and occlusal undercut 133 are located on respective gingival and occlusal sides of the body 106. Undercuts 132, 133 provide areas where an elastic "O"-ring ligature, powerchain, or ligature wire can be secured to retain the archwire 50 in the archwire slot 110. Although not critical for treatment, independent ligation can be useful, for example, when closing gaps (e.g. using a powerchain) or intentionally creating friction (e.g. using elastic ligatures) during the finishing stage of treatment.

In more detail, the door assembly 119 includes a ligating cover 120 and a resilient clip 122, each independently coupled to the hinge 116. The hinge 116 is provided by a simple cylindrical hinge pin 117, operatively coupled to both the clip 122 and the body 106. The hinge pin 116 also has a longitudinal hinge axis 118 that extends along a generally mesial-distal direction, allowing relative rotation of the body 106 about the hinge axis 118 relative to the ligating cover 120 and the clip 122. It is not necessary that the hinge 116 use the hinge pin 117. Alternatively, for example, the body 106 and door assembly 119 could be connected to each other by a flexible polymeric membrane.

The ligating cover 120 is made from a non-staining ceramic material that is optionally the same material used to construct the base 102 and body 106. The ligating cover 120 has a facial surface 123 that has a generally rectangular shape, similar to that of the appliance 100 as a whole when viewed from the facial direction. Optionally and as shown, the facial surface 123 has a vertical alignment groove 124 extending across the facial surface in a generally occlusal-gingival direction. Advantageously, the alignment groove 124 can assist the practitioner in positioning the appliance 100 on the tooth during a bonding procedure.

Referring now to FIG. 5, the clip 122 comprises a shaft portion 126 having an eyelet 128 on its occlusal end and a hook portion 130 on its gingival end, resulting in the clip 122 having a generally "J"-shaped configuration. The eyelet 128 has an aperture 129, allowing the hinge pin 117 to extend through the clip 122. The hook portion 130 functions as a latch by engaging the gingival undercut 132 on the body 106 when the door assembly 119 is in its closed position. In this position, the hook portion 130 is retained by an interference fit with the gingival undercut 132.

The clip 122 is preferably made from a resilient metal alloy, such as stainless steel, titanium, cobalt-chromium alloy (such as manufactured by Elgiloy Specialty Metals, Elgin, Ill.), or a shape-memory alloy such as an alloy of nickel and titanium (e.g. Nitinol). Preferably, the clip 122 is sufficiently resilient so that the shape of the clip 122 when relaxed does not significantly change during the course of treatment. As another option, the clip 122 could be made from any other resilient material known to one skilled in the art, such as a flexible polymer or composite material.

Preferably, the ligating cover 120 and clip 122 interconnected. Moveover, these components may be either adhesively or mechanically coupled to each other. The latter approach is shown in phantom in FIG. 5, where the clip 122 further includes a tab 136 extending outwardly, in a generally facial direction, from the shaft portion 126, and a set pin 138 extends through both the ligating cover 120 and the tab 136. With the ligating cover 120 and the clip 122 mutually fastened by the set pin 138 on one end and the hinge pin 117 on the other end, these components are fixed relative to each other and, as a result, jointly rotate about the hinge axis 118 when operating the appliance 100.

Figure 4:
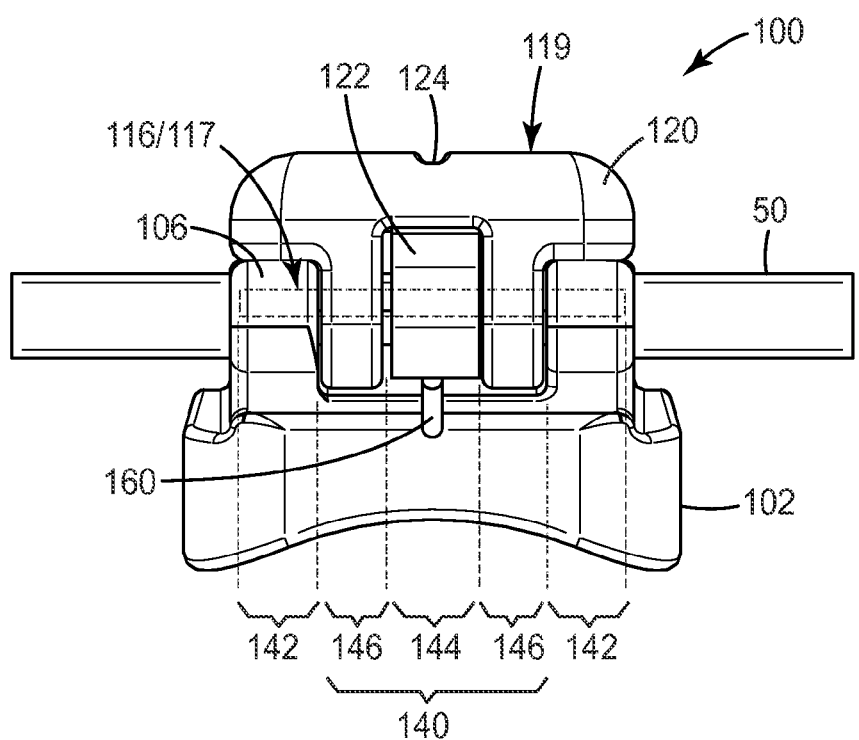
FIG. 4 is an occlusal view of the assembly of FIGS. 1-3, looking toward its occlusal side.

FIG. 4 shows another view of the mechanism of the hinge 116. As shown in phantom, the hinge pin 117 comprises a central section 140 and a pair of end sections 142, the central section 140 extending through the door assembly 119 and the end sections 142 extending through the body 106. More particularly, the central section 140 of the hinge pin 117 has three subsections—a central subsection 144 and a pair of end subsections 146, the central subsection 144 extending through the clip 122 and the end subsections 146 extending through the ligating cover 120. This is merely an exemplary configuration, however, and others are also possible. For example, as an alternative, the central subsection could extends through the ligating cover 120 and the end subsections 146 could extend through the clip 122.

Two additional characteristics of the appliance 100 warrant mention.

First, the directionality of the hinge mechanism, as shown in the figures, can help minimize the chance of accidentally opening the door assembly 119 during mastication, since the door assembly 119 opens towards a direction away from the occlusal teeth surfaces. It should be understood, however, that the occlusal and gingival directions could easily be reversed, if desired, without affecting the operation of the appliance 100.

Figure 2:
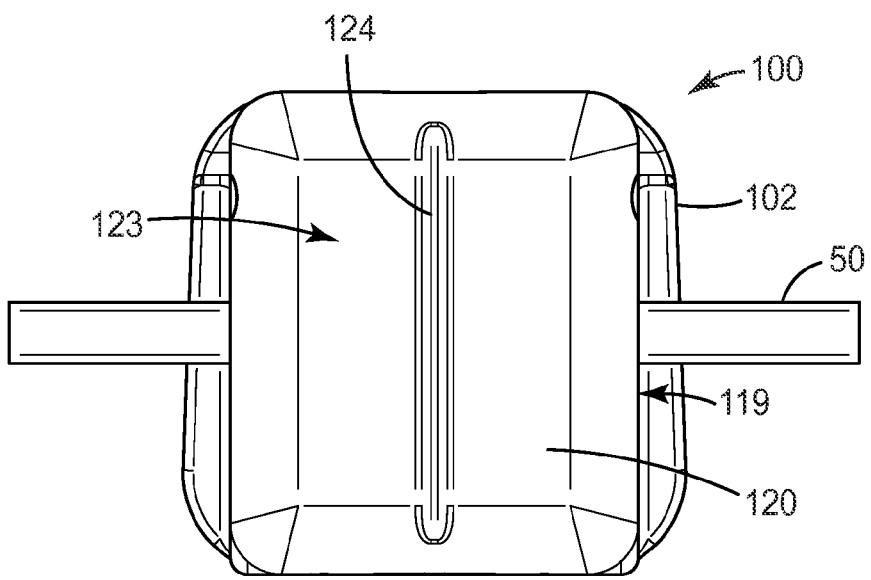
FIG. 2 is a plan view of the assembly of FIG. 1, looking toward its facial side.
Figure 3:
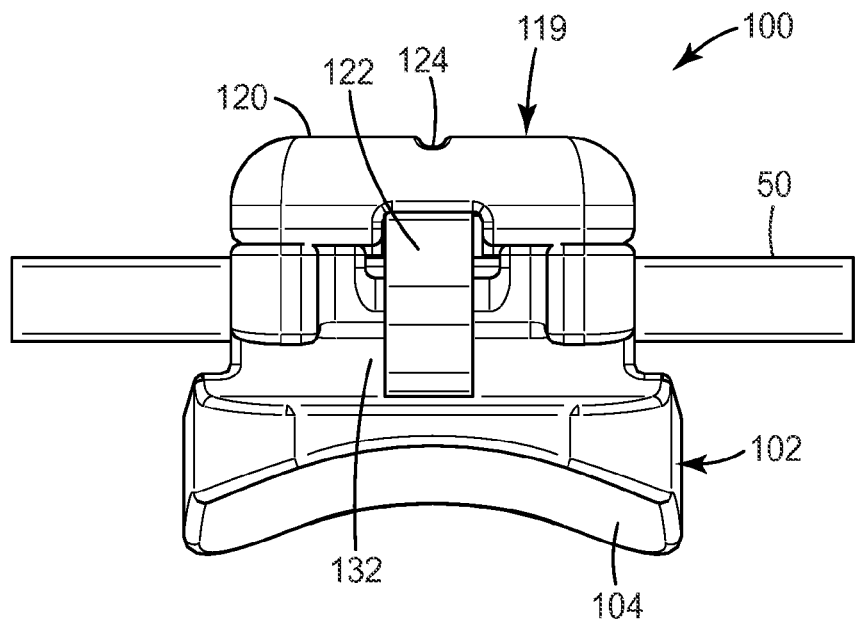
FIG. 3 is a gingival view of the assembly of FIGS. 1-2, looking toward its gingival side.

Second, the aesthetics of the appliance 100 is greatly enhanced by virtue of the ligating cover 120. The ligating cover 120 has a mesial-distal width that is at least that of the clip 122, and thus substantially obscures the clip 122 when the door assembly 119 is in its closed position. As illustrated in FIG. 2, for example, the ligating cover 120 extends over the facial surfaces of the clip 122, causing the clip 122 to be obscured when viewed from the facial direction.

Beginning with the door assembly 119 in its closed position as shown in FIGS. 1-5, the appliance 100 can be operated by inserting the pointed tip of a hand instrument into the gingival undercut 132 next to the hook portion 130 of the clip 122. Then, by engaging the lingual-facing edge of the ligating cover 120 and then applying a gentle force in the facial direction, the terminal end of the hook portion 130 will elastically deflect toward the gingival direction, releasing the clip 122 from its interference fit with the undercut 132. With continued nudging with the hand instrument, the entire door assembly 119 can be easily pivoted about the hinge axis 118 until it reaches the configuration shown in FIG. 6. In this position, access to the archwire slot 110 is allowed whereby archwire 50 can be removed and/or replaced as the practitioner sees fit. Subsequently, reversing the forces on the appliance 100 above can cause the door assembly 119 to pivot back to its natural closed position to obstruct access to the archwire slot 110. Conveniently, the door assembly 119 can be closed using the tip of a finger without need for a hand instrument.

The door assembly 119 can also be opened by inserting into the undercut 132 a flat instrument, having a tip shaped similarly to that of a flat-head screwdriver, and then rotating the instrument along its longitudinal axis. The rotary motion advantageously allows the flat instrument to cam open the door assembly 319 while reducing the risk of hyperextending the same.

Preferably, the force required to open the door assembly 119 is sufficiently low to enable easy operation by a practitioner but also sufficiently high such that the door assembly 119 does not spontaneously disengage during normal patient activity that occurs during treatment, such as chewing and toothbrushing. Preferably, the threshold amount of upward (facial) force applied at the gingival undercut 132 to open the door assembly is at least about 0.9 newtons (0.2 lbf), at least about 2.2 newtons (0.5 lbf), or at least about 4.4 newtons (1 lbf). The threshold force is preferably up to about 5.3 newtons (1.2 lbf), up to about 6.7 newtons (1.5 lbf), or up to about 8.9 newtons (2 lbf).

FIG. 6 shows the appliance 100 with the door assembly 119 fully opened, revealing further aspects of the ligating cover 120, clip 122, and body 106 ordinarily hidden during treatment. As shown, upper and lower channels 150, 152 extend along occlusal-gingival directions on the lingual-facing surface of the ligating cover 120 and the facial-facing surface of the body 106, respectively. With the door assembly 119 closed, the clip 122 is sandwiched between the ligating cover 120 and the body 106, the clip 122 at least partially residing in one or both of the channels 150, 152. Optionally and as shown, the side walls of the channels 150, 152 closely conform to the mesial and distal sides of the clip 122, and help prevent mesial or distal excursion of the clip 122 as the door assembly 119 is opened and closed.

Significantly, the clip 122 does not abut against the upper channel 150 of the ligating cover 120 when in its relaxed configuration. Instead, as shown in FIGS. 5 and 6, the clip 122 is suspended alongside the ligating cover 120 such that a narrow air gap 154 extends along substantially all of the occlusal-gingival length of the channel 150 between the ligating cover 120 and the clip 122. As shown in FIG. 5, when a sufficiently large archwire is received in the archwire slot 110, the clip 122 can resiliently deflect away from the bottom wall 112 of the archwire slot 110 and at least partially into the air gap 154. As a result of this elastic deformation, the ligation provided by the clip 122 becomes "active," characterized by the clip 122 exerting a continuous force toward a generally lingual direction on the archwire 50 during the course of treatment.

"Active ligation" (as opposed to "passive ligation") occurs when a slotted orthodontic appliance imparts a continuous force urging the archwire toward the bottom wall (or sometimes side wall) of the slot. In later stages of treatment, when larger-sized square and rectangular archwires are typically used, "actively" seating these wires into the bracket slot can result in a more effective expression of the appliance prescription. In theory, active ligation can better transmit, for example, torque and rotational forces to the teeth. Another potential benefit of active ligation is the effect of storing some of the therapeutic force in the clip, as well as in the archwire. Some practitioners believe, in general terms, that a given wire will thus have its range of facial-lingual action increased and, therefore, produce more effective alignment than it would in a passively-ligated configuration.

Preferably, the facial-gingival dimension of the archwire slot (with the door assembly 119 in its closed position) enables the appliance 100 to provide active ligation when the archwire 50 exceeds a certain pre-determined facial-lingual cross-sectional dimension. The facial-gingival dimension could also be based on enabling active ligation when there is at least some pre-determined degree of angular deviation between the archwire slot 110 and archwire 50. In some embodiments, the archwire slot 110 has a facial-gingival clearance, as measured between opposing surfaces of the bottom wall 112 and the clip 122 when the door assembly 119 is closed, of at least about 640 micrometers (25 mil), at least about 660 micrometers (26 mil), or at least about 690 micrometers (27 mil). The facial-gingival clearance could be up to about 710 micrometers (28 mil), up to about 740 micrometers (29 mil), or up to about 840 micrometers (33 mil).

The facial-lingual width of the air gap 154 determines, in part, the range of archwire motion and/or size dimensions over which the active ligation is possible. It may be advantageous, in some cases, to use a larger width for the air gap 154 where it is desired to shift the balance between the amount of force provided by deflection of the clip 122 and the amount of force provided through deflection the archwire 50. The air gap 154 can have, for example, a facial-lingual thickness of at least about 25 micrometers (1 mil), at least about 50 micrometers (2 mil), or at least about 80 micrometers (3 mil). The air gap 154 could also have a facial-lingual thickness of up to about 250 micrometers (10 mils), up to about 380 micrometers (15 mil), or up to about 510 micrometers (20 mil).

The appliance 100 includes other optional advantageous features. For example, as shown in FIGS. 4 and 6, the appliance 100 also has a debonding groove 160 located on the facial surface 108 of the body and extending along a generally occlusal-gingival direction. The debonding groove 160 approximately bisects the appliance 100 into mesial and distal halves, and can be used to facilitate squeeze debonding of the appliance 100 from the tooth (by inducing a controlled fracture along the debonding groove 160) at the end of treatment. Optionally, such debonding could be carried out by opening the door assembly 119, and then using a suitable instrument (such as How or Weingart pliers) to squeezes the mesial and distal sides of the body 106 toward each other. Further options and advantages of squeeze debonding of the appliance 100 can be found in issued U.S. Pat. No. 5,439,379 (Hansen).

In another exemplary embodiment, FIGS. 7-11 show an orthodontic appliance 200 engaged to an archwire 50' and having many of the same features described with respect to appliance 100. The appliance 200, however, offers some added benefits as will be described below.

Figure 7:
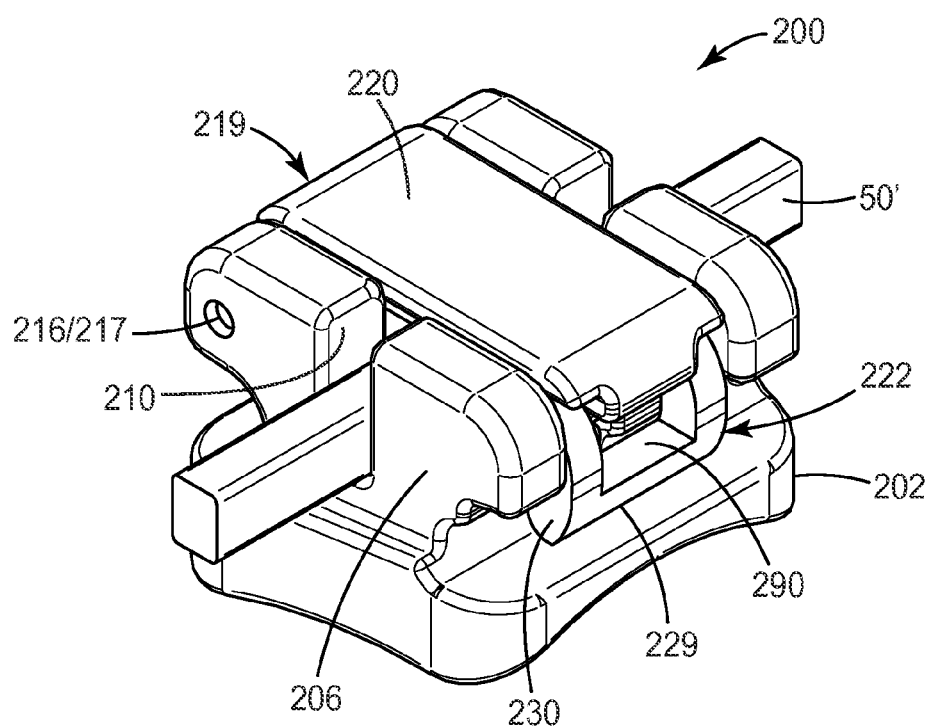
FIG. 7 is a perspective view of an orthodontic assembly including an appliance engaged to an archwire segment according to another embodiment, looking toward its facial, mesial, and gingival sides.

Referring to FIG. 7, the appliance 200 has a base 202 and a body 206 similarly configured to those shown for the appliance 100 in FIGS. 1-6. Appliance 200 also has a door assembly 219 that includes a ligating cover 220 and resilient clip 222, the door assembly 219 jointly pivoting about a hinge 216 using hinge pin 217. The clip 222 differs significantly from the clip 122 in its overall size and shape, and manner of connecting to the ligating cover 220.

Figure 9:
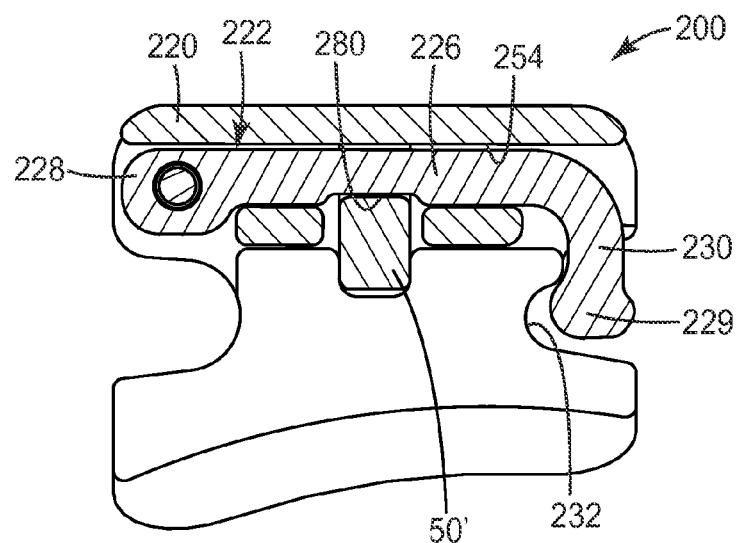
FIG. 9 is a cross-sectional view of the assembly of FIGS. 7-8, looking toward its mesial side.
Figure 10:
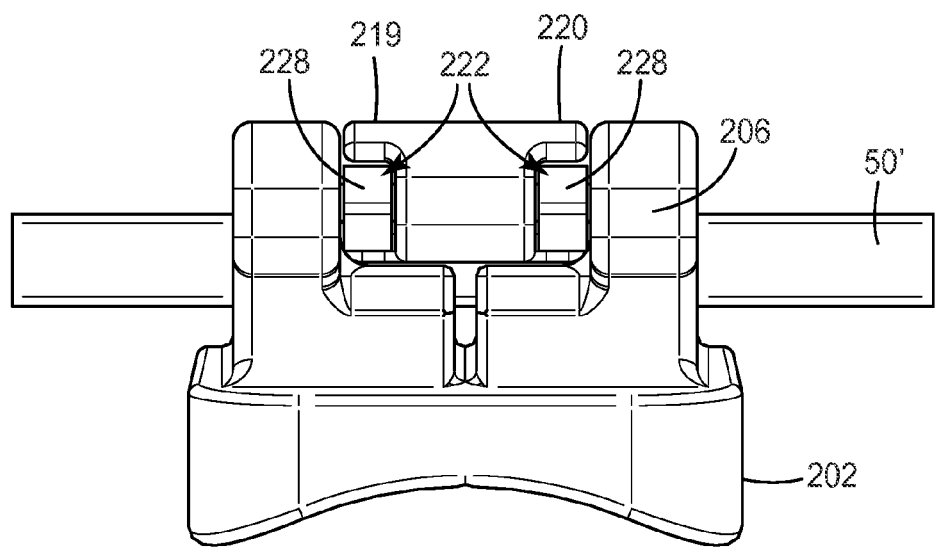
FIG. 10 is an occlusal view of the assembly of FIGS. 7-9, looking toward its occlusal side.
Figure 11:
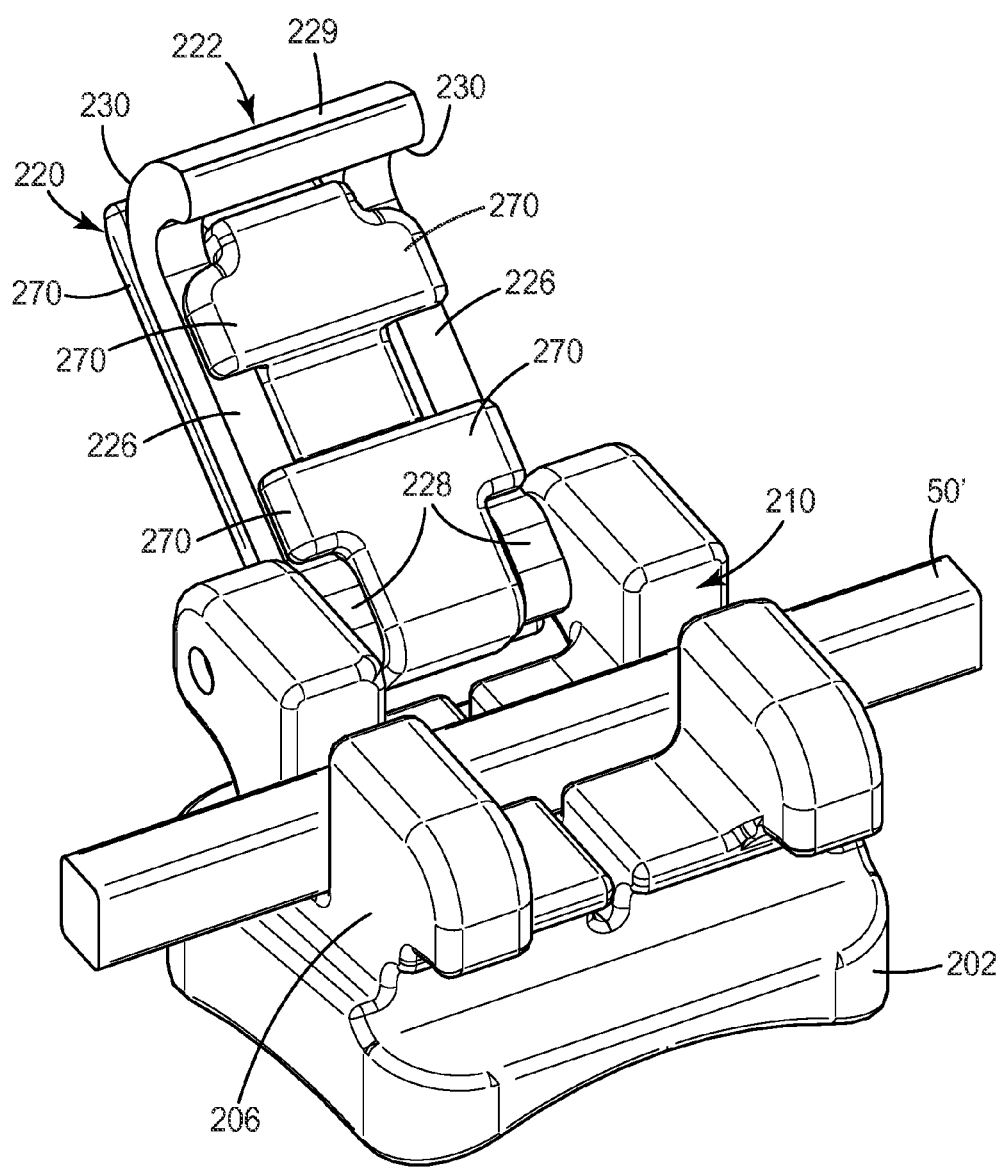
FIG. 11 is a perspective view of the assembly of FIGS. 7-10, showing the appliance in an opened configuration and looking toward its facial, mesial, and gingival sides.

First, and as shown in the opened configuration shown in FIG. 11, the clip 222 has a generally "U"-shaped configuration, having two generally parallel shaft portions 226, each of the shaft portions 226 terminating in an eyelet 228 fastened to the hinge pin 217, as shown in FIGS. 9 and 11. On the opposite end of each shaft portion 226 is a hook portion 230 having characteristics similar to the earlier described clip 122. Unlike the clip 122, however, the clip 222 also has a generally straight connector portion 229 extending along a generally mesial-distal direction and interconnecting the terminal ends of the hook portions 230 as shown in FIG. 11.

Second, the shaft portions 226 of the clip 222 are mechanically coupled to the ligating cover 220 by a set of flanges 270 that are located on the ligating cover 220 and extend along opposite-facing sides of the clip 222. The depicted embodiment in FIG. 11 shows four short flanges 270 on the lingual side of the clip 222 and two long flanges on the facial side of the clip 222. By consequence of the interference fit between these components, the ligating cover 220 and the clip 222 jointly rotate about the hinge pin 217 during operation of the appliance 200. Although not illustrated, other methods of coupling the ligating cover 220 and clip 222 are possible, including use of a set pin or adhesive.

One of the advantages of using a non-planar clip, as embodied in the clip 222, is increased mesial-distal length along which the archwire 50' can contact the door assembly 219. Because the door assembly 219 can engage the archwire 50' at two locations that are spaced apart from each other along a mesial-distal direction, it is possible to reduce angular slop in the archwire 50' and achieve greater rotation control than otherwise achievable by engaging the archwire 50' at a single location. Like in the appliance 100, the clip 222 of the appliance 200 can provide for active ligation when the archwire 50' has a sufficiently large facial-lingual dimension.

Figure 8:
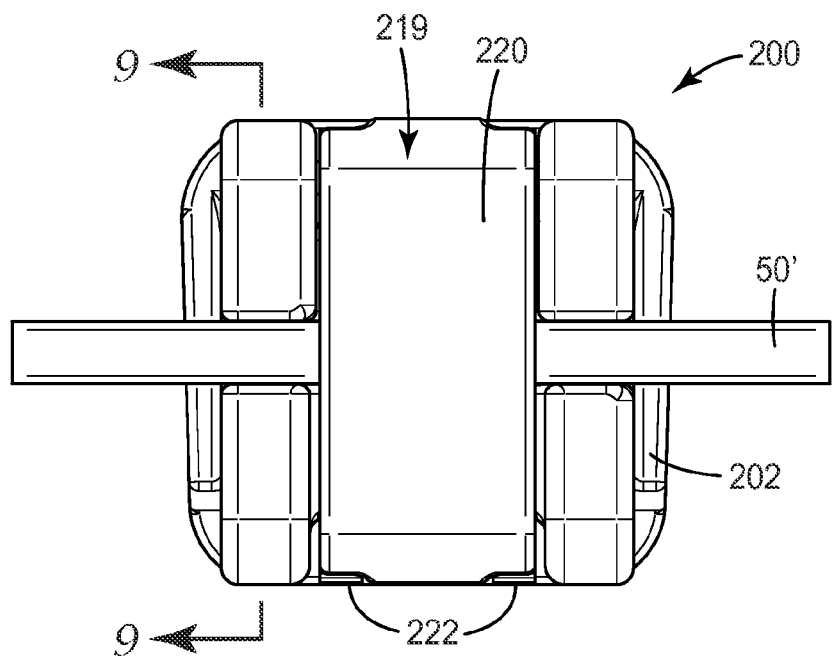
FIG. 8 is a plan view of the assembly of FIG. 7, looking toward its facial side.

The cross-sectional view of FIG. 9, taken along the section 9-9 in FIG. 8, shows in greater detail the interaction between the appliance 200 and the archwire 50'. As shown, the terminal end of the hook portions 230, along with the connector portion 229, can precisely snap into an undercut 232 located on the gingival side of the body 206. As a further option, the lingual underside of the clip 222 could include a shallow relief 280 (as shown) to tailor further the degree of space available for the archwire 50'. It is also possible, if desired, to adjust the spacing of the air gap 254 between the clip 222 and the facing surface of the ligating cover 220 to increase or decrease the degree of force that can be provided by the appliance 200 in an active ligation configuration. Similar benefits apply with respect to the appliance 100.

Another benefit, as shown in FIG. 7, is the creation of a generally rectangular recess 290, located on the gingival side of the appliance 200, to assist in operating the appliance 200. The recess 290 is collectively defined by the hook portion 230, connector portion 229, and the ligating cover 220. The recess 290 is sufficiently sized to accommodate the tip of a hand instrument for operating the door assembly 219. The recess 290 is advantageously located at or near the mesial-distal midpoint of the gingival side of the appliance 200, allowing forces imparted by a hand instrument to be distributed evenly to the hook portions 230 and shaft portions 226.

Figure 12:
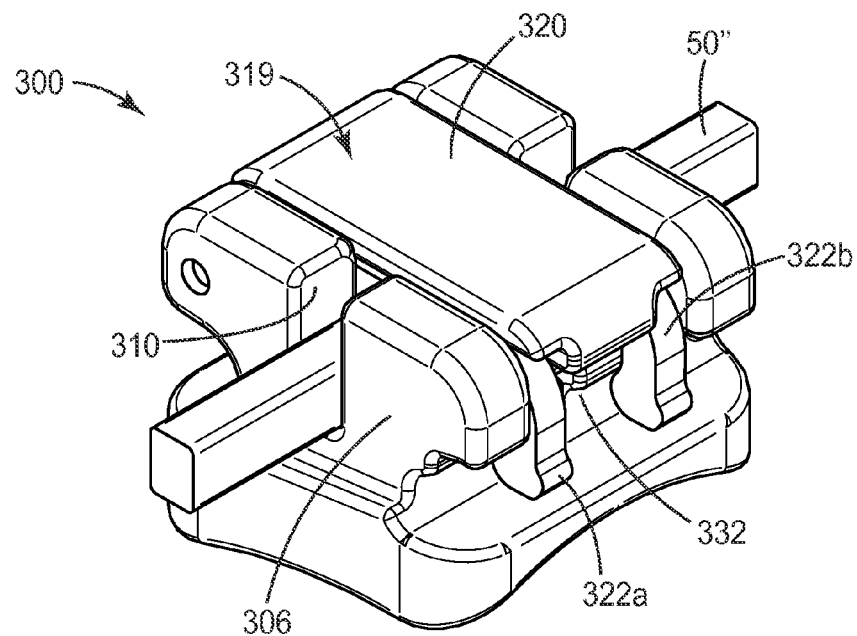
FIG. 12 is a perspective view of an orthodontic assembly including an appliance engaged to an archwire segment according to still another embodiment, looking toward its facial, mesial, and gingival sides.
Figure 13:
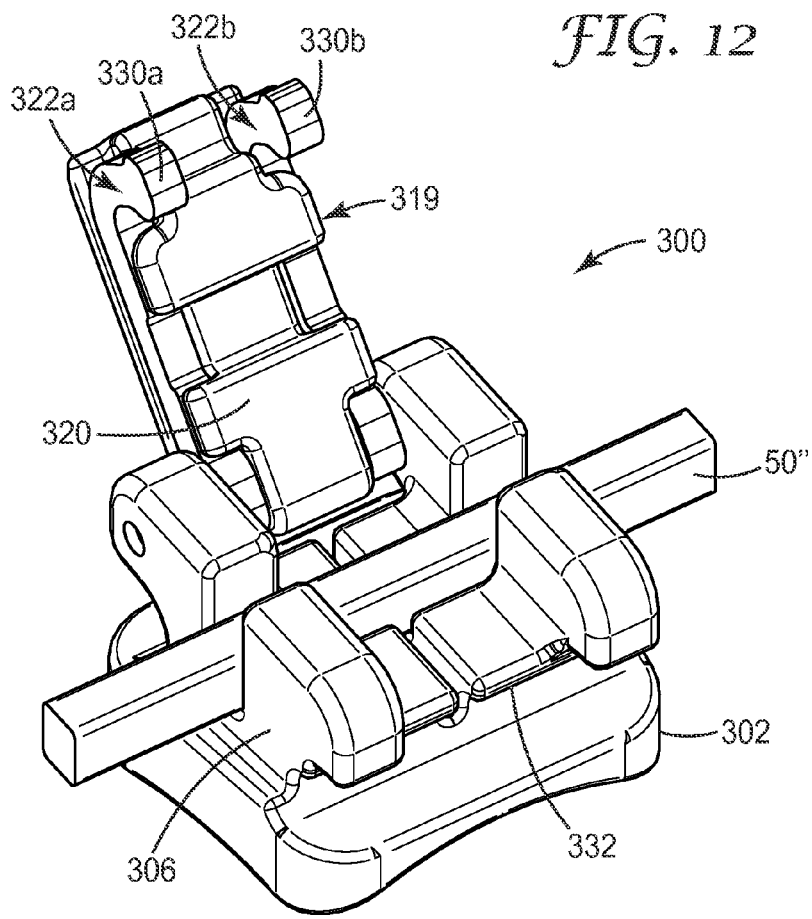
FIG. 13 is a perspective view of the assembly of FIG. 12, showing the appliance in an opened configuration, and looking toward its facial, mesial, and gingival sides.

FIGS. 12 and 13 show an appliance 300 engaging an archwire 50", according to still another embodiment, in respective open and closed configurations. The appliance 300 has many of the same features as the appliance 200, including a base 302, body 306 with an archwire slot 310, and door assembly 319. However, unlike the appliances 100, 200, the appliance 300 includes a door assembly 319 having a pair of planar, generally "J"-shaped clips 322a, 322b disposed on the mesial and distal sides of a ligating cover 320, respectively. As shown in FIG. 13, each clip 322a, 322b has a hook portion 330a, 330b for releasably engaging an undercut 332 on the gingival side of the body 306.

Certain potential benefits can be realized with a dual-clip configuration. For example, using a pair of planar clips 322a, 322b instead of a single integrated clip can help facilitate manufacturing. Further, the lack of a connector portion between the clips 322a, 322b provides for a slightly larger recess to accommodate a hand instrument for operating the door assembly 319. Finally, implementing a pair of clips instead of a singular clip can also decrease the effective force required to open the door assembly 319, since it is possible for clips 322a, 322b to disengage individually from corresponding undercut 332.

It is to be understood that many aspects of the appliances 200, 300 are analogous to those of the appliance 100 as previously described. Accordingly, corresponding options and features of the appliances 200, 300 will not be repeated.

One of the unexpected advantages of the provided appliances 100, 200, 300 relates to the much lower labial force needed to open the door assembly 119, 219, 319 when applied at the terminal end of the clip 122, 222, 322, compared with the force needed when applied at the archwire slot 110, 210, 310. It was discovered that the clip 122, 222, 322, when deflected into a curved shape by the archwire, adopts a configuration that substantially increases the force required to disengage the clip 122, 222, 322 from the corresponding undercut 132, 232, 332. As a result of this deflection, the actual force required to open the door assembly 119, 219, 319 is substantially greater at the archwire slot 110, 210, 310 than would be predicted geometrically by treating the door assembly 119, 219, 319 as a simple lever arm.

The forces needed to unlatch the door assembly 119, 219, 319 can be quantified as follows. Unlatching the door assembly 119, 219, 319 by pivoting it from its closed to its open position requires a first minimum force applied to the clip 122, 222, 322 at the archwire slot 110, 210, 310 in a direction substantially perpendicular to the bottom wall of the archwire slot 110, 210, 310. Furthermore, the act of unlatching the door assembly 119, 219, 319 requires a second minimum force when applied to the clip 122, 222, 322 at its hook portion 130, 230, 330a, 330b (in the same direction). In some embodiments, the first minimum force exceeds the second minimum force by a factor of about 2.5, about 3, about 3.5, about 4, about 4.5, about 5, or about 6.

For the foregoing reasons, the configuration of the clip 122, 222, 322 provides a novel answer to the technical challenge of allowing the practitioner to easily open the door assembly 119, 219, 319 using a low threshold force at the gingival end of the door assembly 119, 219, 319 (e.g. using the tip of a hand instrument at the recess 290), while avoiding spontaneous disengagement of the archwire by imposing a relatively high threshold force to open the door assembly 119, 219, 319 at the archwire slot 110, 210, 310.

The comparative forces above can be simulated using, for example, finite element analysis ("FEA"). In the exemplary appliance 100, the threshold facial force required to open the door assembly 119 was simulated using ANSYS FEA software (ANSYS, Inc., Canonsburg, Pa.) to be about 4.9 newtons (1.1 lbf) at the set pin 138 of the clip 122, compared to about 28 newtons (6.2 lbf) at the archwire slot 110. This approximate 6:1 force ratio compares to a ratio of about 2:1 force ratio based on linear distance from the hinge axis 118.

Various additional embodiments A-Z are provided below:

A. An orthodontic appliance having: a base having an outer surface adapted for bonding to a tooth; a body extending outwardly from the base in a direction away from the outer surface of the base and having an elongated archwire slot therein extending along a generally mesial-distal direction, the archwire slot having a bottom wall and a pair of sidewalls; a hinge coupled to the body and having a hinge axis extending along a generally mesial-distal direction; and a door assembly having: a ceramic ligating cover; and a resilient clip coupled to one or both of the ligating cover and the hinge, where the door assembly is pivotable along the hinge axis between an open position allowing access to the archwire slot and a closed position obstructing access to the archwire slot, the ligating cover substantially obscuring the clip when the door assembly is in its closed position.

B. The appliance of embodiment A, further having an air gap extending between the ligating cover and the clip, the air gap providing space for the clip to elastically deform in a direction away from the bottom wall of the archwire slot in active ligation.

C. The appliance of embodiment B, where the air gap has a facial-lingual thickness ranging from about 25 micrometer to about 510 micrometers.

D. The appliance of embodiment C, where the air gap has a facial-lingual thickness ranging from about 50 micrometers to about 380 micrometers.

E. The appliance of embodiment D, where the air gap has a facial-lingual thickness ranging from about 80 micrometers to about 250 micrometers.

F. The appliance of any of embodiments A-E, where one or both of the base and body comprise a ceramic material.

G. The appliance of embodiment F, where the ceramic material includes polycrystalline alumina H. The appliance of any of embodiments A-G where the clip includes a shape-memory alloy.

I. The appliance of any of embodiments A-H where the hinge includes a hinge pin operatively coupled to both the clip and the body, where the hinge axis is the longitudinal axis of the hinge pin.

J. The appliance of embodiment I, where the hinge pin includes a central section and a pair of opposing end sections, the central section extending through the door assembly and the end sections extending through the body.

K. The appliance of embodiment J, where the central section includes a central subsection and a pair of end subsections, the first subsection extending through the clip and the end subsections extending through the ligating cover.

L. The appliance of embodiment J, where the central section includes a central subsection and a pair of end subsections, where the central subsection extends through the ligating cover and the end subsections extend through the clip.

M. The appliance of any of embodiments A-L, where the clip includes a shaft portion and a hook portion joined at one end of the shaft portion, thereby providing a generally "J"-shaped configuration.

N. The appliance of embodiments M, where the clip further includes a tab extending outwardly from the shaft portion and further having a set pin extending through both the ligating cover and the tab to allow the ligating cover and the clip to jointly rotate about the hinge axis.

O. The appliance of embodiment M, further having an undercut on either an occlusal or gingival side of the body, the hook portion retained by an interference fit with the undercut when the door assembly is in its closed position.

P. The appliance of embodiment O, the door assembly further having a recess collectively defined by the hook portion and the ligating cover when the door assembly is in its closed position, where the recess is sufficiently sized to accommodate the tip of a hand instrument for operating the door assembly.

Q. The appliance of embodiment P, where toggling the door assembly from its closed to its open position requires a first minimum force when applied to the door assembly at the archwire slot and a second minimum force when applied to the door assembly at the recess, the first minimum force exceeding the second minimum force by a factor of about 2.5.

R. The appliance of embodiment Q, where the first minimum force exceeds the second minimum force by a factor of about 4.

S. The appliance of embodiment R, where the first minimum force exceeds the second minimum force by a factor of about 6.

T. The appliance of any of embodiments A-S, further having a plurality of flanges located on the ligating cover and extending along opposite-facing sides of the clip whereby the ligating cover and the clip jointly rotate about the hinge axis.

U. The appliance of any of embodiments A-T, where the ligating cover has a mesial-distal width of at least the mesial-distal width of the clip.

V. The appliance of any of embodiments A-U, where the archwire slot has a facial-lingual clearance ranging from about 640 to about 740 micrometers, as measured between opposing surfaces of the bottom wall and the clip, when the door assembly is in its closed position.

W. A method of activating an archwire in an orthodontic appliance having a body with an elongated archwire slot having a bottom wall and pair of side walls therein and a latched door assembly including a resilient clip provided alongside a ligating cover presenting an air gap therebetween, and a hinge interconnecting the body and door assembly, the method including: placing the archwire in the archwire slot; and pivoting the door assembly about the hinge until the clip latches to the body, the clip resiliently deflecting into the air gap while the clip applies a compressive force urging the archwire towards the bottom of the archwire slot.

X. The method of embodiment W, where unlatching the door assembly from its closed to its open position requires a first minimum force applied at the archwire slot in a direction substantially perpendicular to the bottom wall and a second minimum force applied at the terminal end of the clip also in a direction substantially perpendicular to the bottom wall, the first minimum force exceeding the second minimum force by a factor of about 2.5.

Y. The appliance of embodiment X, where the first minimum force exceeds the second minimum force by a factor of about 4.

Z. The appliance of embodiment Y, where the first minimum force exceeds the second minimum force by a factor of about 6.

All of the patents and patent applications mentioned above are hereby expressly incorporated into the present disclosure. The foregoing invention has been described in some detail by way of illustration and example for purposes of clarity and understanding. However, various alternatives, modifications, and equivalents may be used and the above description should not be taken as limiting in the scope of the invention which is defined by the following claims and their equivalents.

What is claimed is:

1. An orthodontic appliance comprising:
   a base having an outer surface adapted for bonding to a tooth;
   a body extending outwardly from the base in a direction away from the outer surface of the base and having an elongated archwire slot therein extending along a generally mesial-distal direction, the archwire slot having a bottom wall and a pair of sidewalls;
   a hinge coupled to the body and having a hinge axis extending along a generally mesial-distal direction; and
   a door assembly comprising:
      a ligating cover; and
      a resilient clip coupled to one or both of the ligating cover and the hinge and deflectable in a facial direction away from the bottom wall, wherein the door assembly is pivotable along the hinge axis between an open position allowing access to the archwire slot and a closed position obstructing access to the archwire slot, the ligating cover substantially obscuring the clip when the door assembly is in its closed position, and
   wherein the clip extends across and in a facial direction from the archwire slot when the door assembly is in its closed position.

2. The appliance of claim 1, further comprising an air gap extending between the ligating cover and the clip, the air gap providing space for the clip to elastically deform in a direction away from the bottom wall of the archwire slot in active ligation.

3. The appliance of claim 2, wherein the air gap has a facial-lingual thickness ranging from about 25 micrometer to about 510 micrometers.

4. The appliance of claim 3, wherein the clip is coextensive with a portion of the ligation cover disposed above the bottom wall of the archwire slot when the door assembly is in its closed position.

5. The appliance of claim 2, wherein the portion of the clip extending across the archwire slot elastically deforms in a direction away from the bottom wall.

6. The appliance of claim 1 wherein the hinge comprises a hinge pin operatively coupled to both the clip and the body, wherein the hinge axis is the longitudinal axis of the hinge pin.

7. The appliance of claim 6, wherein the hinge pin comprises a central section and a pair of opposing end sections, the central section extending through the door assembly and the end sections extending through the body.

8. The appliance of claim 7, wherein the central section comprises a central subsection and a pair of end subsections, the central subsection extending through the clip and the end subsections extending through the ligating cover.

9. The appliance of claim 7, wherein the central section comprises a central subsection and a pair of end subsections, wherein the central subsection extends through the ligating cover and the end subsections extend through the clip.

10. The appliance of claim 1, wherein the clip comprises a shaft portion and a hook portion joined at one end of the shaft portion, thereby providing a generally "J"-shaped configuration.

11. The appliance of claim 10, wherein the clip further comprises a tab extending outwardly from the shaft portion and further comprising a set pin extending through both the ligating cover and the tab to allow the ligating cover and the clip to jointly rotate about the hinge axis.

12. The appliance of claim 10, further comprising an undercut on either an occlusal or gingival side of the body, the hook portion retained by an interference fit with the undercut when the door assembly is in its closed position.

13. The appliance of claim 12, the door assembly further comprising a recess collectively defined by the hook portion and the ligating cover when the door assembly is in its closed position, wherein the recess is sufficiently sized to accommodate the tip of a hand instrument for operating the door assembly.

14. The appliance of claim 13, wherein toggling the door assembly from its closed to its open position requires a first minimum force when applied to the door assembly at the archwire slot and a second minimum force when applied to the door assembly at the recess, the first minimum force exceeding the second minimum force by a factor of about 2.5.

15. The appliance of claim 14, wherein the first minimum force exceeds the second minimum force by a factor of about 6.

16. The appliance of claim 1, further comprising a plurality of flanges located on the ligating cover and extending along opposite-facing sides of the clip whereby the ligating cover and the clip jointly rotate about the hinge axis.

17. A method of activating an archwire in an orthodontic appliance having a body with an elongated archwire slot having a bottom wall and pair of side walls therein and a latched door assembly including a resilient clip provided alongside a ligating cover presenting an air gap therebetween, and a hinge interconnecting the body and door assembly, the method comprising:
   placing the archwire in the archwire slot; and
   pivoting the door assembly about the hinge until the clip latches to the body, the clip resiliently deflecting into the air gap while the clip applies a compressive force urging the archwire towards the bottom of the archwire slot.

18. The method of claim 17, wherein unlatching the door assembly from its closed to its open position requires a first minimum force applied at the archwire slot in a direction substantially perpendicular to the bottom wall and a second minimum force applied at the terminal end of the clip also in a direction substantially perpendicular to the bottom wall, the first minimum force exceeding the second minimum force by a factor of about 2.5.

19. The appliance of claim 18, wherein the first minimum force exceeds the second minimum force by a factor of about 6.

20. An orthodontic appliance comprising:
a base having an outer surface adapted for bonding to a tooth;
a body extending outwardly from the base in a direction away from the outer surface of the base and having an elongated archwire slot therein extending along a generally mesial-distal direction, the archwire slot having a bottom wall and a pair of sidewalls, and an undercut on either an occlusal or gingival side of the body;
a hinge coupled to the body and having a hinge axis extending along a generally mesial-distal direction; and
a door assembly pivotable along the hinge axis between an open position allowing access to the archwire slot and a closed position obstructing access to the archwire slot, door assembly comprising,
a clip coupled to the hinge and extending across the bottom wall of the archwire slot when the door assembly is in its closed position, the clip including a hook portion retained by an interference fit with the undercut when the door assembly is in its closed position, wherein the clip is deflectable in a facial direction away from the bottom wall and such deflection of the clip substantially increases the force required to disengage the hook portion from the undercut.

21. The appliance of claim 20, wherein toggling the door assembly from its closed to its open position requires a first minimum force when applied to the door assembly at the archwire slot and a second minimum force when applied to the door assembly at the recess, the first minimum force exceeding the second minimum force by a factor of about 2.5.

* * * * *